(12) United States Patent
Kosuge et al.

(10) Patent No.: US 10,758,196 B2
(45) Date of Patent: Sep. 1, 2020

(54) RADIATION IMAGING APPARATUS, CONTROL METHOD FOR RADIATION IMAGING APPARATUS, AND PROGRAM

(71) Applicant: CANON KABUSHIKI KAISHA, Tokyo (JP)

(72) Inventors: Asato Kosuge, Kawasaki (JP); Taro Hiroike, Yamato (JP); Hideki Nonaka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 816 days.

(21) Appl. No.: 15/379,315

(22) Filed: Dec. 14, 2016

(65) Prior Publication Data

US 2017/0164916 A1    Jun. 15, 2017

(30) Foreign Application Priority Data

Dec. 15, 2015  (JP) .................................. 2015-244651
Dec. 18, 2015  (JP) .................................. 2015-248028

(51) Int. Cl.
*A61B 6/00*    (2006.01)
*G16H 40/67*   (2018.01)
*G16H 40/63*   (2018.01)
*G16H 30/20*   (2018.01)

(52) U.S. Cl.
CPC ............ *A61B 6/467* (2013.01); *A61B 6/4283* (2013.01); *A61B 6/465* (2013.01); *A61B 6/54* (2013.01); *G16H 30/20* (2018.01); *G16H 40/63* (2018.01); *G16H 40/67* (2018.01)

(58) Field of Classification Search
CPC ............ A61B 6/465; A61B 6/467; A61B 6/54; A61B 6/4283; G16H 30/20; G16H 40/63; G16H 40/67; G06F 19/321
See application file for complete search history.

(56) References Cited

U.S. PATENT DOCUMENTS 7,119,841 B1 * 10/2006 Sako ........................ A61B 6/00
                                                                348/333.05
2002/0080918 A1 * 6/2002 Sako ..................... A61B 6/548
                                                                378/115
2005/0157848 A1 * 7/2005 Miyauchi ................ A61B 6/56
                                                                378/207
2005/0244044 A1 * 11/2005 Inoue .................... G06T 7/0012
                                                                382/132

(Continued)

FOREIGN PATENT DOCUMENTS

JP    2006-042965 A    2/2006
JP    2010-051745 A    3/2010

(Continued)

OTHER PUBLICATIONS

Machine translation of JP2012135697 (Year: 2012).*

*Primary Examiner* — David J Makiya
*Assistant Examiner* — Soorena Kefayati
(74) *Attorney, Agent, or Firm* — Canon U.S.A., Inc. IP Division

(57) ABSTRACT

A radiation imaging apparatus includes a radiation detection unit that acquires a radiation image, a decision unit that decides whether or not the radiation image meets a decision criterion of success or failure of imaging, and a storage unit that associates and stores the radiation image and a result of the decision.

19 Claims, 8 Drawing Sheets

(56) References Cited

U.S. PATENT DOCUMENTS

| | | | | |
|---|---|---|---|---|
| 2005/0256743 A1* | 11/2005 | Dale | ................ | G16H 40/20 705/2 |
| 2009/0003679 A1* | 1/2009 | Ni | ................ | A61B 6/463 382/132 |
| 2009/0080734 A1* | 3/2009 | Moriya | ................ | G06F 19/321 382/128 |
| 2009/0262892 A1* | 10/2009 | Haras | ................ | A61B 6/463 378/62 |
| 2009/0279672 A1* | 11/2009 | Reiner | ................ | A61B 6/581 378/207 |
| 2009/0279764 A1* | 11/2009 | Kaji | ................ | G06T 7/0012 382/132 |
| 2010/0104066 A1* | 4/2010 | Foos | ................ | A61B 6/463 378/62 |
| 2010/0104167 A1* | 4/2010 | Sakaguchi | ................ | A61B 6/12 382/132 |
| 2011/0049370 A1* | 3/2011 | Yoshida | ................ | A61B 6/548 250/354.1 |
| 2011/0058727 A1* | 3/2011 | Tsujii | ................ | G06T 7/11 382/132 |
| 2011/0110496 A1* | 5/2011 | Foos | ................ | A61B 6/463 378/98.5 |
| 2011/0311026 A1* | 12/2011 | Lalena | ................ | A61B 6/542 378/98.5 |
| 2012/0196258 A1* | 8/2012 | Geijsen | ................ | G16H 30/40 434/262 |
| 2013/0114793 A1* | 5/2013 | Ohta | ................ | A61B 5/0059 378/63 |
| 2013/0121556 A1* | 5/2013 | Matsumoto | ................ | A61B 6/50 382/132 |
| 2013/0184537 A1* | 7/2013 | Konuma | ................ | A61B 5/0033 600/300 |
| 2013/0329860 A1* | 12/2013 | Nonaka | ................ | G16H 40/67 378/91 |
| 2013/0336458 A1* | 12/2013 | Arima | ................ | A61B 6/563 378/98 |
| 2014/0112447 A1* | 4/2014 | Semba | ................ | A61B 6/545 378/98 |
| 2014/0168276 A1* | 6/2014 | Takeda | ................ | G09G 5/373 345/671 |
| 2014/0276056 A1* | 9/2014 | Ohta | ................ | A61B 8/467 600/440 |
| 2014/0321614 A1* | 10/2014 | Yamada | ................ | A61B 6/4405 378/62 |
| 2015/0039553 A1* | 2/2015 | Becker | ................ | A61B 6/481 706/52 |
| 2015/0066431 A1* | 3/2015 | Zheng | ................ | A61B 6/586 702/183 |
| 2015/0117607 A1* | 4/2015 | Hayashi | ................ | A61B 6/463 378/62 |
| 2015/0356271 A1* | 12/2015 | Kozuka | ................ | G06F 16/5838 705/2 |
| 2015/0359498 A1* | 12/2015 | Zou | ................ | A61B 6/542 378/62 |
| 2016/0350925 A1* | 12/2016 | Moon | ................ | A61B 6/5241 |
| 2017/0311920 A1* | 11/2017 | Hiroshige | ................ | G06F 19/00 |

FOREIGN PATENT DOCUMENTS

| | | | |
|---|---|---|---|
| JP | 2010-094290 | A | 4/2010 |
| JP | 2010-137058 | A | 6/2010 |
| JP | 2010-137059 | A | 6/2010 |
| JP | 2011-030661 | A | 2/2011 |
| JP | 2012135697 | * | 7/2012 |
| JP | 2013-090986 | A | 5/2013 |
| JP | 2013-102851 | A | 5/2013 |
| JP | 2013-104826 | A | 5/2013 |
| JP | 2013-233420 | A | 11/2013 |
| JP | 2015-084937 | A | 5/2015 |
| JP | 2015-191557 | A | 11/2015 |
| JP | 2015-226105 | A | 12/2015 |

* cited by examiner

FIG. 6

| IMAGE | PORTION TO BE IMAGED | COUNTER | SUCCESS OR FAILURE OF IMAGING | IMAGING TIME | IMAGING TECHNOLOGIST NO. | IMAGING RADIATION DOSE |
|---|---|---|---|---|---|---|
| IMAGE 1 | CHEST FRONT | 001 | SUCCESS | 11:00 | 001 | 10 |
| IMAGE 2 | CHEST SIDE | 002 | SUCCESS | 11:02 | 002 | 20 |
| IMAGE 3 | THORACIC VERTEBRAE | 003 | FAILURE | 11:04 | 003 | 30 |
| IMAGE 4 | THORACIC VERTEBRAE | 004 | SUCCESS | 11:06 | 004 | 40 |

FIG. 7A

| IMAGE | PORTION TO BE IMAGED | COUNTER/ IMAGING TECHNOLOGIST NO. | IMAGING TIME | IMAGING RADIATION DOSE |
|---|---|---|---|---|
| IMAGE 1 | CHEST FRONT | 001 | 11:00 | 10 |
| IMAGE 2 | CHEST SIDE | 002 | 11:02 | 20 |
| IMAGE 3 | THORACIC VERTEBRAE | 003 | 11:04 | 30 |
| IMAGE 4 | THORACIC VERTEBRAE | 004 | 11:06 | 40 |

FIG. 7B

| IMAGE | PORTION TO BE IMAGED | COUNTER/ IMAGING TECHNOLOGIST NO. | IMAGING TIME | IMAGING RADIATION DOSE |
|---|---|---|---|---|
| IMAGE 1 | CHEST FRONT | 001 | 11:00 | 10 |
| IMAGE 2 | CHEST SIDE | 002 | 11:02 | 20 |
| IMAGE 3 | THORACIC VERTEBRAE | 003 | 11:04 | 30 |
| IMAGE 4 | THORACIC VERTEBRAE | 004 | 11:06 | 40 |

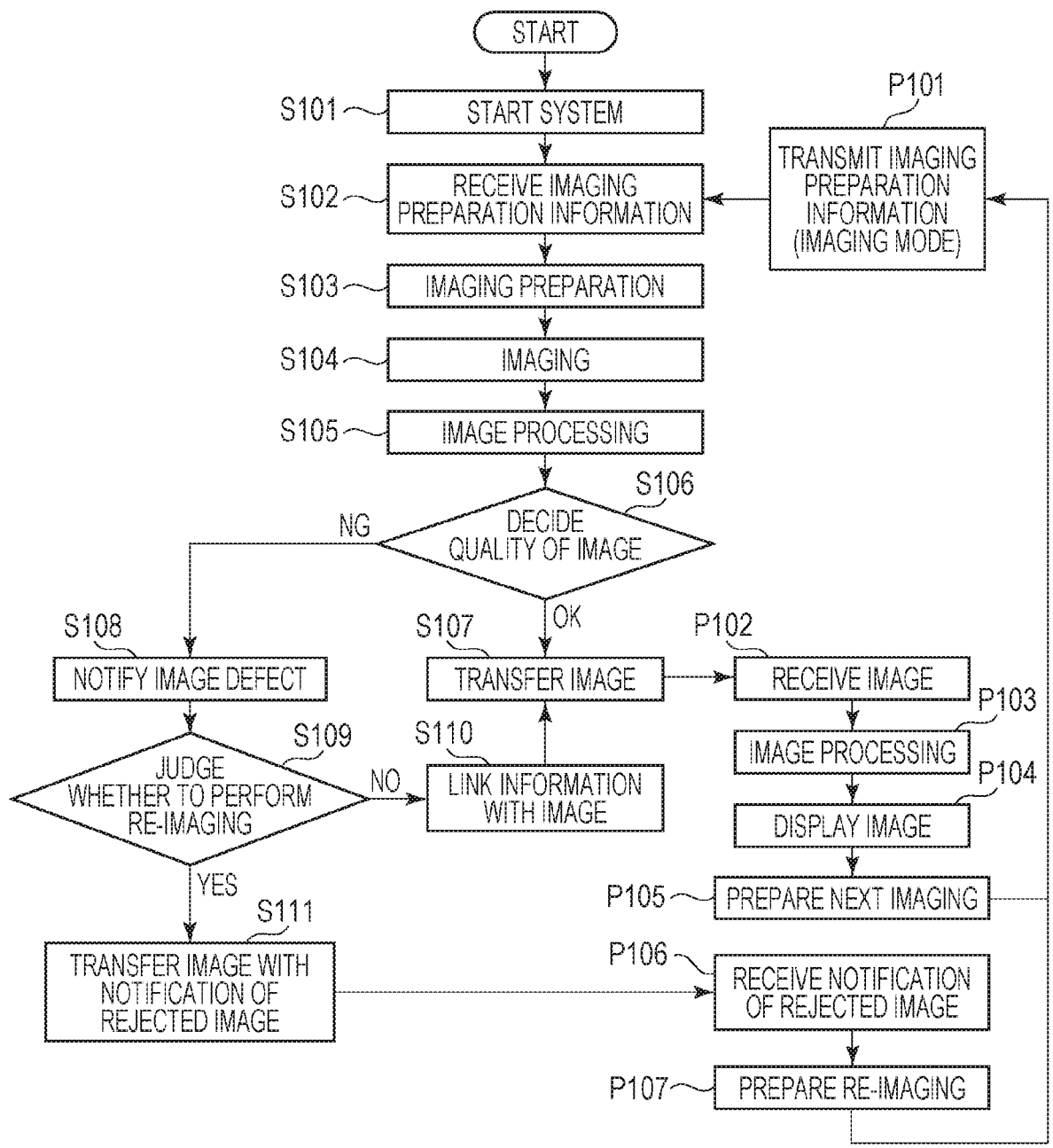

RADIATION IMAGING APPARATUS, CONTROL METHOD FOR RADIATION IMAGING APPARATUS, AND PROGRAM

BACKGROUND

Field of the Disclosure

The present disclosure relates to a radiation imaging apparatus, a control method for the radiation imaging apparatus, and a program.

Description of the Related Art

Imaging using radiation is used in various fields, and a radiation imaging apparatus that acquires a radiation image obtained by digitizing a radiation image obtained through radiation imaging is widespread in a medical field. The radiation imaging apparatus is reduced in size and weight, and thus is portable as a portable radiation imaging apparatus and is able to perform imaging in various places.

Japanese Patent Laid-Open No. 2010-137059 discloses a configuration in which a radiation image, an imaging condition, and the like are displayed for each imaging on a display unit of a radiation imaging apparatus as a configuration for checking success or failure of imaging of the radiation image. According to the configuration of Japanese Patent Laid-Open No. 2010-137059, a user is able to decide success or failure of imaging by visually checking the radiation image, the imaging condition, and the like displayed for each imaging on the display unit.

However, with the configuration of Japanese Patent Laid-Open No. 2010-137059, the user is difficult to decide success or failure of imaging unless the user checks the radiation image, the imaging condition, and the like for each imaging displayed on the display unit. For example, in a case of an imaging state where the user is difficult to check the display unit, for example, the display unit of the radiation imaging apparatus is covered by a subject, the user is difficult to visually check the radiation image, the radiation condition, and the like on the display unit of the radiation imaging apparatus. In such a case, for displaying the radiation image, the imaging condition, and the like on the display unit of an information processing apparatus, the radiation imaging apparatus needs to be connected to the information processing apparatus through wired communication or wireless communication, so that complicated work is required for the user.

SUMMARY

A radiation imaging apparatus according to one or more aspects of the present disclosure includes, a radiation detection unit configured to acquire a radiation image, a decision unit configured to decide whether or not the radiation image meets a decision criterion of success or failure of imaging, and a storage unit configured to associate and store the radiation image and a result of the decision.

A control method for a radiation imaging apparatus according to another aspect of the disclosure is a control method for a radiation imaging apparatus that has a radiation detection unit configured to acquire a radiation image, the control method includes the steps of deciding whether or not the radiation image meets a decision criterion for deciding success or failure of imaging, and storing the radiation image and a decision result at the deciding step in the storage unit in association with each other.

Thus, one or more aspects of the present disclosure provides a radiation imaging technique by which a decision result of success or failure of imaging of a radiation image is able to be obtained.

Further features of the present disclosure will become apparent from the following description of exemplary embodiments with reference to the attached drawings.

BRIEF DESCRIPTION OF THE DRAWINGS

FIG. 6 illustrates an example of association of imaging information with a decision result of a radiation image according to one or more aspects of the present disclosure.

FIGS. 7A and 7B each illustrates a display example of a display unit of the radiation imaging apparatus according to one or more aspects of the present disclosure.

FIG. 8 is a flowchart illustrating an operation of a radiation imaging system according to one or more aspects of the present disclosure.

DESCRIPTION OF THE EMBODIMENTS

First Exemplary Embodiment

A first exemplary embodiment of the disclosure will be described below in detail with reference to FIG. 1 to FIGS. 7A and 7B. However, constituent components described in the exemplary embodiment merely provide an example, so that the technical scope of the disclosure is determined by the scope of claims and is not limited by the following individual exemplary embodiments.

Figure 1:
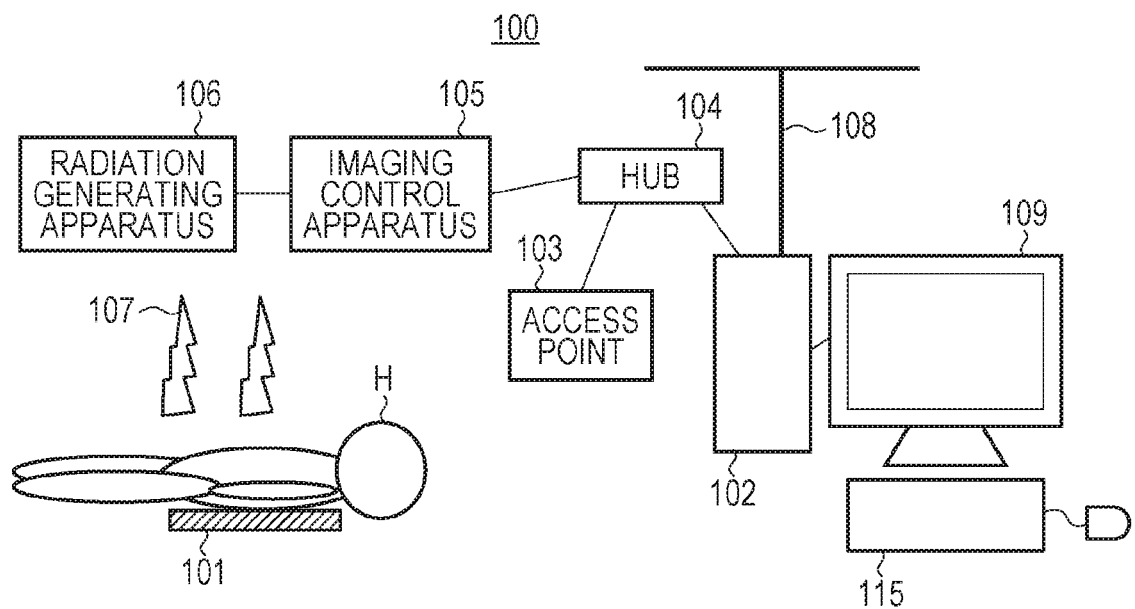
FIG. 1 illustrates a configuration example of a radiation imaging system according to one or more aspects of the present disclosure.

FIG. 1 illustrates a configuration example of a radiation imaging system 100 in the first exemplary embodiment. As illustrated in FIG. 1, the radiation imaging system 100 has a radiation imaging apparatus 101, an information processing apparatus 102, an access point 103, a HUB 104, an imaging control apparatus 105, and a radiation generating apparatus 106. The radiation imaging apparatus 101 captures a radiation image on the basis of radiation 107 which is transmitted through a subject H. The radiation imaging apparatus 101 is configured by a portable radiation imaging apparatus. Note that, a configuration of the imaging control apparatus 105 may be included inside the radiation imaging apparatus 101. In this case, the imaging control apparatus 105 functions as an imaging control unit that controls imaging of the radiation imaging apparatus 101.

The information processing apparatus 102 is able to perform display control for displaying a radiation image captured by the radiation imaging apparatus 101 on a display unit 109 of the information processing apparatus 102 and output an imaging instruction based on an imaging mode input through an operation unit 115. The information processing apparatus 102 is also able to perform image processing for the radiation image captured by the radiation imaging apparatus 101 and display the radiation image subjected to the image processing on the display unit 109.

The access point 103 is a radio wave repeater connected to a wireless communication device. The access point 103 and the radiation imaging apparatus 101 are able to communicate with each other through wireless communication. The HUB 104 is a communication connection apparatus for connecting a plurality of network devices, and the radiation imaging apparatus 101 is able to be connected to the information processing apparatus 102 through the access point 103 and the HUB 104.

The imaging control apparatus 105 has a communication circuit using wireless communication or wired communication, and the imaging control apparatus 105 is able to be connected to the HUB 104, the radiation imaging apparatus 101, and the radiation generating apparatus 106. Moreover, the imaging control apparatus 105 is able to be connected to the information processing apparatus 102 through the HUB 104. The imaging control apparatus 105 acquires information indicating states of the radiation imaging apparatus 101 and the radiation generating apparatus 106 through the communication circuit and monitors the states of the apparatuses. The imaging control apparatus 105 controls the radiation generating apparatus 106 and the radiation imaging apparatus 101 on the basis of an imaging instruction output from the information processing apparatus 102.

The radiation generating apparatus 106 has a radiation tube and a rotor for accelerating electrons with a high voltage to cause them to strike an anode, thus generating the radiation 107, for example, such as X-ray, and the radiation generating apparatus 106 radiates the radiation 107 under control of the imaging control apparatus 105. Note that, the radiation 107 may be any of α-ray, β-ray, γ-ray, and X-ray. Under control of the imaging control apparatus 105, the radiation imaging apparatus 101 captures an image of the subject H to which the radiation 107 is radiated. An intra-hospital LAN 108 is a local area network built in a hospital. The radiation imaging system 100 is able to be connected to a radiation information system (RIS), a hospital information system (HIS), and a picture archiving communication system (PACS) through the intra-hospital LAN 108.

In the radiation imaging system 100 illustrated in FIG. 1, the radiation generating apparatus 106 radiates the radiation 107 under control of the imaging control apparatus 105 and the radiation 107 radiated from the radiation generating apparatus 106 is radiated to the subject H who is a patient. Under control of the imaging control apparatus 105, the radiation imaging apparatus 101 detects the radiation 107 transmitted through the subject H at the timing in synchronization with the radiation of the radiation 107 and generates a radiation image on the basis of a detection result.

The radiation imaging apparatus 101 has, for example, a pixel of detecting radiation in a configuration of a pixel array detecting the radiation 107. A radiation detection unit 15 configured by the pixel array starts acquisition of a radiation image on the basis of the detection of the radiated radiation. Upon radiation of the radiation 107 from the radiation generating apparatus 106, the radiation detection unit 15 of the radiation imaging apparatus 101 is able to operate in an automatic detection mode of automatically accumulating an image signal (electric charge) on the basis of the detection result of the pixel for detecting radiation and generating a radiation image. Even in a case where the imaging control apparatus 105 is not provided in the configuration of the radiation imaging system 100, when the radiation 107 is radiated from the radiation generating apparatus 106, the radiation imaging apparatus 101 is able to operate in the automatic detection mode to automatically accumulate an image signal (electric charge) and generate a radiation image. Thereby, the radiation imaging apparatus 101 is able to perform imaging in synchronization with the radiation of the radiation 107 from the radiation generating apparatus 106.

A method for detecting radiation of the radiation 107 is not limited to the above, and may be a method for monitoring an amount of change in a bias line and a signal line forming the pixel array. Note that, the radiation imaging system 100 is able to execute imaging in a plurality of imaging modes. Here, the plurality of imaging modes have at least a first imaging mode and a second imaging mode.

The first imaging mode is an imaging mode in which imaging is performed in a state where communication between the radiation imaging apparatus 101 and the information processing apparatus 102 is able to be performed through a wired or wireless manner. The radiation imaging apparatus 101 performs control for transferring an acquired radiation image for each imaging to the information processing apparatus 102. The information processing apparatus 102 displays the transferred radiation image on the display unit 109.

The second imaging mode is an imaging mode in which imaging is performed in a state where communication between the radiation imaging apparatus 101 and the information processing apparatus 102 is not able to be performed through a wired or wireless manner. The radiation imaging apparatus 101 does not transfer an acquired radiation image to the information processing apparatus 102 for each imaging but accumulates acquired radiation images in a storage unit 14 to collectively transfer them to the information processing apparatus 102.

Here, the first imaging mode includes at least a synchronous imaging mode and an asynchronous imaging mode (automatic detection mode). The synchronous imaging mode is an imaging mode of exchanging an electrical synchronizing signal or the like for matching the imaging timing between the radiation imaging apparatus 101 and the radiation generating apparatus 106. Matching the imaging timing means matching timing of radiating the radiation and a time period in which electric charges are accumulated by the radiation detection unit 15. In the asynchronous imaging mode, a synchronizing signal is not exchanged between the radiation imaging apparatus 101 and the radiation generating apparatus 106, but the radiation imaging apparatus 101 itself detects incidence of the radiation and starts accumulation of electric charges.

In the second imaging mode, the radiation imaging apparatus 101 itself detects incidence of the radiation, and stores a radiation image in the storage unit 14 in the radiation imaging apparatus 101 without transferring the radiation image to the information processing apparatus 102 for each imaging. Thus, the second imaging mode may be said as a mode in which the radiation imaging apparatus 101 is able to capture a plurality of radiation images in a state of being independent from the information processing apparatus 102. When the aforementioned configuration of the imaging control apparatus 105 is provided inside the radiation imaging apparatus 101, the imaging control apparatus 105 functions as an imaging control unit that controls imaging of the radiation imaging apparatus 101. The imaging control unit is able to control imaging in the first imaging mode or the second imaging mode while controlling a communication unit 2.

Figure 2:
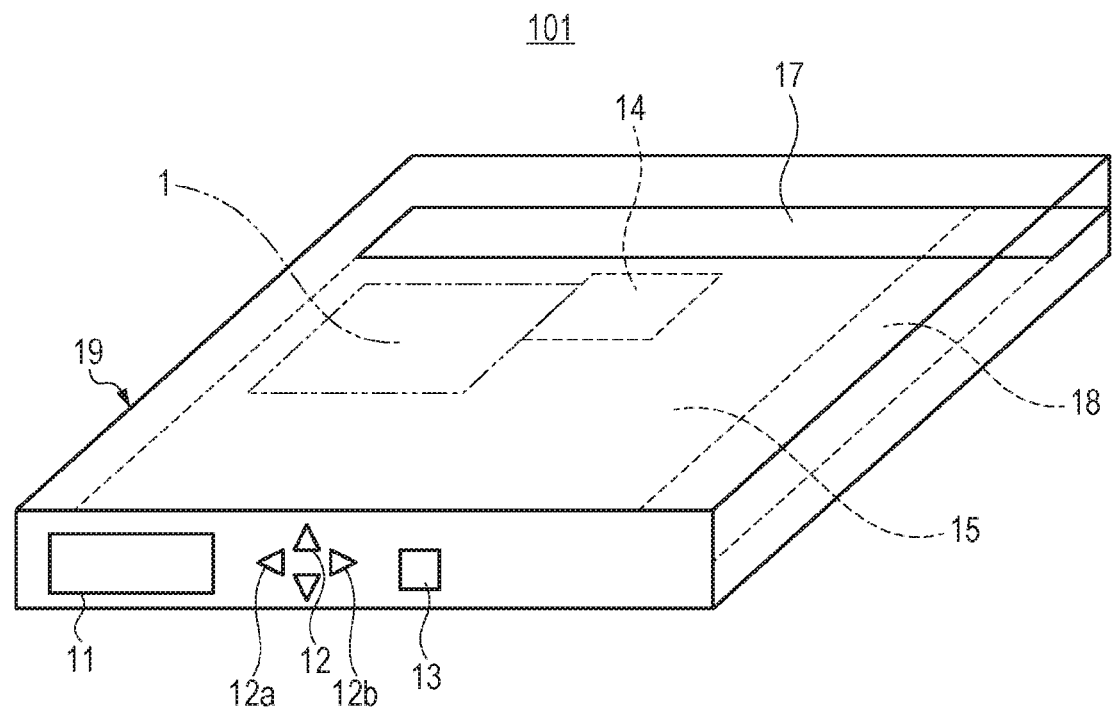
FIG. 2 illustrates a configuration example of a radiation imaging apparatus according to one or more aspects of the present disclosure.
Figure 3:
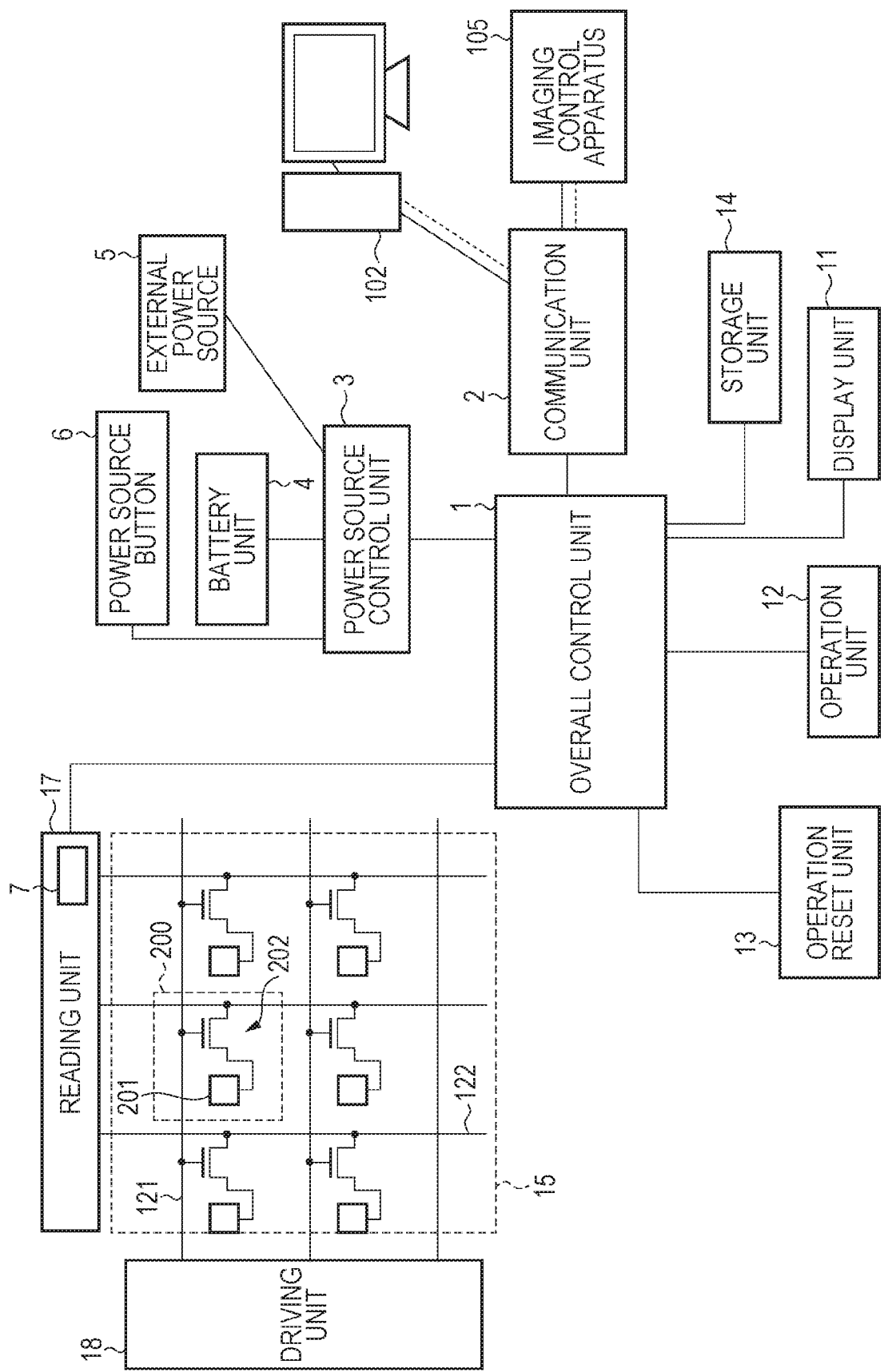
FIG. 3 illustrates a configuration example of the radiation imaging apparatus according to one or more aspects of the present disclosure.
Figure 4:
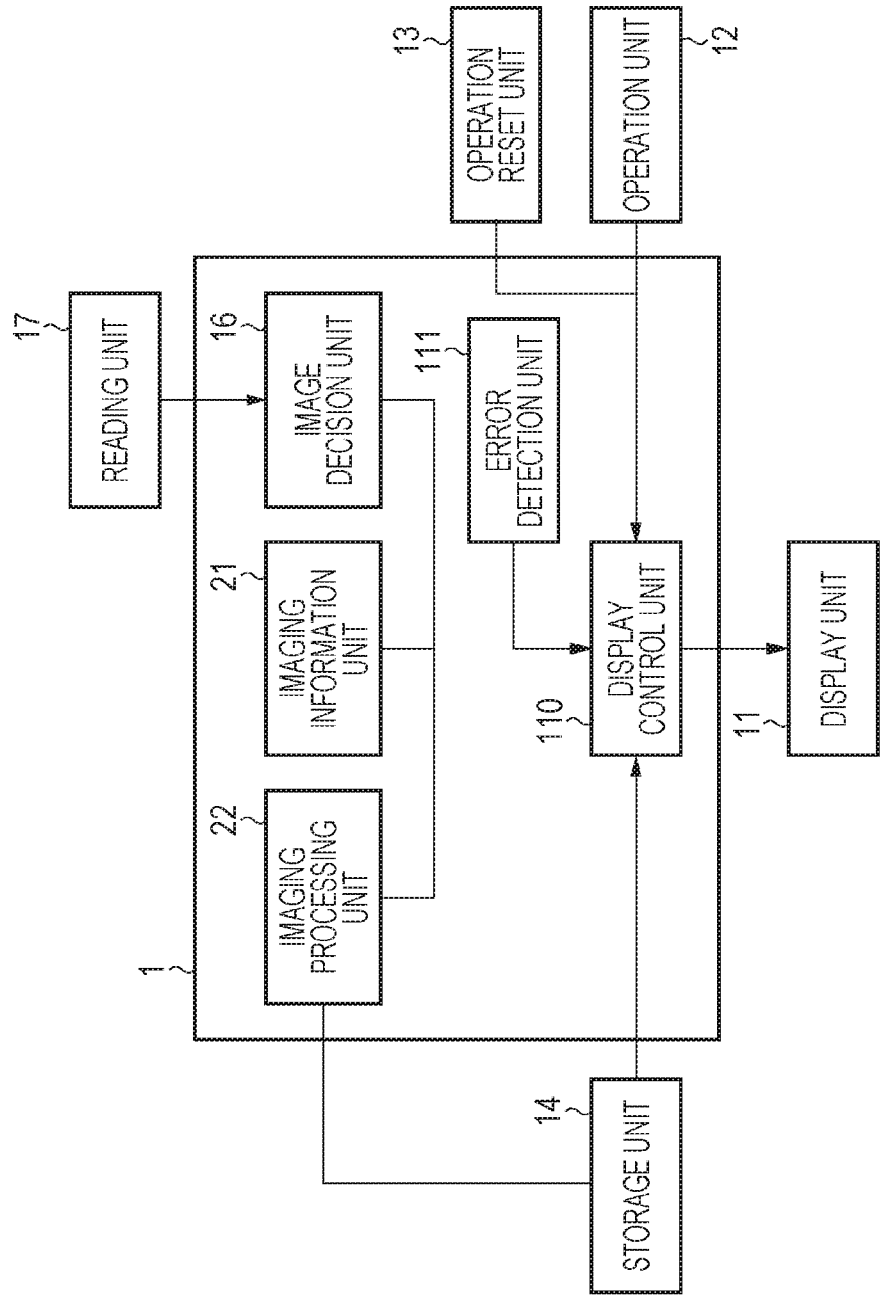
FIG. 4 illustrates an internal configuration example of an overall control unit according to one or more aspects of the present disclosure.

FIGS. 2 and 3 each illustrates a configuration example of the portable radiation imaging apparatus 101 in the present exemplary embodiment. FIG. 4 is a block diagram illustrating an internal configuration example of an overall control unit 1 illustrated in FIG. 3. As illustrated in the schematic configuration of FIG. 2, a display unit 11, an operation unit 12, and an operation reset unit 13 are arranged on a side portion of a housing 19 of the radiation imaging apparatus 101. The storage unit 14, the radiation detection unit 15, the overall control unit 1, a reading unit 17, and a driving unit 18 are arranged inside the housing 19 of the radiation imaging apparatus 101. The storage unit 14 and the overall control unit 1 are arranged on a lower surface side of the housing 19, and the radiation detection unit 15 is arranged on an upper surface side of the housing 19. The radiation detection unit 15 is held inside the housing 19 so as to be able to receive the radiation 107 incident on the upper surface side of the housing 19.

The display unit 11 has a function of displaying information, which is stored in the storage unit 14, under display control by a display control unit 110 (FIG. 4). By arranging the display 11 on the side surface portion of the housing 19, it is possible to prevent the display unit 11 from being covered by a subject during imaging and achieve improvement in visibility of a user.

The operation unit 12 is an input unit that receives a user operation, and the operation unit 12 is able to be configured by a button, a dial, a joystick, a touch sensor, a touch pad, and the like. In order to enable the user to perform a user operation for the operation unit 12 while viewing a display of the display unit 11, the operation unit 12 is arranged in line with the display unit 11. On the basis of a user operation through the operation unit 12 and display control of the display control unit 110, the display unit 11 switches a display of information indicating success or failure of imaging (success in imaging or failure in imaging) of a radiation image, imaging information about the radiation image, a thumbnail image of the radiation image, or the like.

The operation reset unit 13 is an input unit that receives a user operation for returning the display content of the display unit 11 to the state before the operation of the operation unit 12. The operation unit 12 and the operation reset unit 13 are arranged in line with each other in FIG. 2 so that the user operation (reset operation) for returning the switched display of the display unit 11 to the state before switching is able to be performed easily by the user operation for the operation unit 12. The operation unit 12 and the operation reset unit 13 are arranged in line with the display unit 11 so that the user operation for the operation unit 12 and the operation reset unit 13 is able to be performed while viewing the display of the display unit 11.

Note that, a part of a plurality of input units of the operation unit 12 may be allocated to a function of the operation resent unit 13. For example, references signs 12a and 12b in FIG. 2 denote a plurality of input units of the operation unit 12, and the input unit 12a may function to switch the display of the display unit 11 and the input unit 12b may function to perform a reset operation of the operation reset unit 13. By allocating a part of the plurality of input units of the operation unit 12 to the function of the operation reset unit 13 in this manner, the operation reset unit 13 arranged as a separate configuration does not need to be provided in the housing 19 of the radiation imaging apparatus 101. In a case where the display unit 11 is configured by a touch sensor, when the user touches the display unit 11, it is possible to switch the display content or return the display content to the state before switching. In this case, functions similar to those of the operation unit 12 and the operation reset unit 13 are also able to be implemented by the touch sensor of the display unit 11.

The storage unit 14 associates and stores a captured radiation image and information indicating success or failure of imaging (success in imaging or failure in imaging) of the radiation image. The storage unit 14 is also able to associate and store the radiation image, information indicating success or failure of imaging (success in imaging or failure in imaging) of the radiation image, and imaging information including an imaging condition of the radiation image. The imaging information includes, for example, at least any one of identification information of the radiation image, a portion of a subject to be imaged, the number of times of imaging (counter), an imaging time, identification information of a technologist who performs an imaging operation, an imaging radiation dose, and identification information of the subject.

The display control unit 110 is able to acquire the information, which is stored in the storage unit 14, at any timing. The information of the storage unit 14 is output to the display control unit 110 in response to an instruction of the display control unit 110. The display control unit 110 controls the display of the display unit 11 on the basis of the information stored in the storage unit 14. The storage unit 14 is configured to be capable of reading and writing, and is able to be detachably mounted, like a SD card or a flash memory, in the radiation imaging apparatus 101. Note that, the configuration of the present exemplary embodiment is not limited to such an example, and the storage unit 14 is able to be configured by a non-volatile memory.

The radiation detection unit 15 detects the radiation 107, which is transmitted through the subject H, as an image signal (electric charge). As illustrated in FIG. 3, pixels 200 each of which outputs a signal corresponding to incident light are arranged in the radiation detection unit 15 in an array (two-dimensional region). Photoelectric conversion elements of the pixels 200 convert light, which is converted by a phosphor, into image signals (electric charges) that are electric signals, and capacitors of the pixels 200 accumulate the image signals (electric charges). In this manner, the radiation detection unit 15 constitutes a radiation imaging unit that detects the radiation 107 transmitted through the subject H and acquires the image signals (electric charges).

As illustrated in FIG. 3, the driving unit 18 supplies a driving signal to the pixels 200 for each line through a signal line 121 in accordance with an instruction from the overall control unit 1. When the driving signal is supplied to the pixels 200 in a certain line by the driving unit 18, switch elements of the pixels 200 are sequentially brought into an on state and the image signals (electric charges) converted by the photoelectric conversion elements are accumulated. The reading unit 17 reads the image signals (electric charges) output to the signal line 122 from the pixels 200 for each row in accordance with an instruction from the overall control unit 1. The reading unit 17 has an analog/digital (A/D) conversion unit 7 (hereinafter, an A/D conversion unit 7), and the reading unit 17 outputs the image signals (electric charges) read from the pixels 200 to the overall control unit 1 through the A/D conversion unit 7.

The A/D conversion unit 7 converts the image signal as an analog signal read from each of the pixels 200 by the reading unit 17 into an image signal as a digital signal, and outputs the digital image signal to the overall control unit 1 as a radiation image. The overall control unit 1 functions as a control unit that performs overall control for the operation of the radiation imaging apparatus 101. A specific configuration of the overall control unit 1 will be described below with reference to FIG. 4.

The communication unit 2 of the radiation imaging apparatus 101 is able to communicate with the external information processing apparatus 102 and imaging control apparatus 105 through wired communication or wireless communication. In FIG. 3, each solid line and each dotted line between the communication unit 2 of the radiation imaging apparatus 101 and each of the information processing apparatus 102 and the imaging control apparatus 105 respectively represent wired communication and wireless communication. The communication unit 2 is also able to perform wireless communication with the access point 103 illustrated in FIG. 1.

A power source control unit 3 converts voltage from a battery unit 4 and an external power source 5 into predetermined voltage, and controls voltage supply to each component of the radiation imaging apparatus 101. The power source control unit 3 performs control of the voltage supply from the battery unit 4 or the external power source 5 and monitoring of a battery residual of the battery unit 4. The battery unit 4 is able to supply the predetermined voltage from a battery under control of the power source control unit 3, and supply the predetermined voltage to each unit of the radiation imaging apparatus 101 through the power source control unit 3. The external power source 5 is able to supply the predetermined voltage from an external power source and supply the predetermined voltage to each unit of the radiation imaging apparatus 101 through the power source control unit 3.

A power source button 6 is a button for switching start and stop of voltage supply from a power source (battery unit 4). For example, when the external power source 5 is not connected, on and off of the voltage supply from the battery unit 4 is able to be switched by an operation of the power source button 6. When the external power source 5 is connected, on and off of the voltage supply from the external power source 5 is able to be switched by an operation of the power source button 6. Note that, on and off of the voltage supply from the external power source 5 may be switched on the basis of whether or not the external power source 5 is connected regardless of the operation of the power source button 6.

FIG. 4 illustrates an internal configuration example of the overall control unit 1. As the internal configuration, the overall control unit 1 has an image decision unit 16, an imaging information unit 21, an imaging processing unit 22, the display control unit 110, and an error detection unit 111. The reading unit 17 outputs an image signal (electric charge) read from the pixel 200 to the overall control unit 1 through the A/D conversion unit 7. In this case, the A/D conversion unit 7 converts the image signal as an analog signal read from the pixel 200 by the reading unit 17 into an image signal as a digital signal, and outputs the digital image signal to the overall control unit 1.

The overall control unit 1 generates a radiation image from the digital image signal. The image decision unit 16 decides whether or not the radiation image meets a decision criterion of success or failure of imaging. That is, the image decision unit 16 decides whether the radiation image generated by the radiation detection unit 15 meets the predetermined decision criterion. In this case, whether or not to meet the predetermined decision criterion is decided on the basis of whether or not to be an image achieving a level sufficiently usable for the purpose of a diagnosis or the like. An example of the decision criterion includes positioning decision, a radiation dose [mAs] when the radiation image is generated, artifact detection, body movement detection for detecting a movement of a subject during imaging, detection of a foreign substance, detection of an impact, error reception from the radiation generating apparatus 106, or the like. The overall control unit 1 may perform various processing for the radiation image. In this case, the image decision unit 16 decides whether or not the radiation image after the processing meets the decision criterion of success or failure of imaging. The processing performed in this case can include, for example, defect correction for correcting a defect of the image, offset correction for correcting offset data of the image, and noise reduction processing for reducing various noises. Note that, the overall control unit 1 may not carry out all the processing for making a diagnosis image, and a part of the processing is able to be performed by the information processing apparatus 102.

The positioning decision is a decision item for deciding whether or not a portion desired to be imaged is included. The image decision unit 16 decides whether or not a relative position between the portion desired to be imaged and the radiation imaging apparatus 101 is appropriate on the basis of the radiation image captured by the positioning decision. The image decision unit 16 can perform, on the basis of magnitude of a pixel value of the radiation image, decision about the radiation dose [mAs] when the radiation image is generated and artifact detection (an amount of generated artifact) on the radiation image. The body movement detection (or blur detection) is processing performed by detecting an amount of shift (edge component) in a certain direction of the radiation image. The image decision unit 16 decides presence or absence of a body movement by checking whether a structure on a line in the image has a strong component in a specific direction. Further, the image decision unit 16 is able to perform detection of misalignment of a grid, decision for false recognition of the front and the back of the radiation imaging apparatus 101, and decision for imaging at inappropriate timing. The image decision unit 16 performs a level decision of the radiation image for deciding whether a radiation dose is excess or insufficient from magnitude of a pixel value of the radiation image. The level decision is processing performed by collecting statistics of luminance data of the entire image and comparing the highest value and the lowest value of luminance to a threshold of each of them. In the level decision, when the number of pixels exceeding the threshold is beyond a fixed range which is set, it is decided that there is a possibility of an image defect.

The image decision unit 16, when the radiation image input from the reading unit 17 meets the decision criterion, decides that the imaging has succeeded, and when the radiation image does not meet the decision criterion, decides that the imaging has failed. For example, when a pixel value of the radiation image is smaller than a pixel value as the decision criterion, when a radiation dose when the radiation image is generated is lower than a radiation dose as the decision criterion, or when a foreign substance, an impact, or error reception is detected from a result of image processing or a detection result of a sensor, the image decision unit 16 decides that the imaging has failed. The image decision unit 16 outputs information indicating a decision result of success or failure of imaging (success in imaging or failure in imaging) of the radiation image and the radiation image input from the reading unit 17 in association with each other.

The imaging information unit 21 retains imaging information about the radiation image acquired in repose to an imaging instruction and outputs the imaging information at predetermined timing. The imaging information includes, for example, at least any one of identification information of the radiation image, a portion of a subject to be imaged, the number of times of imaging (counter), an imaging time, identification information of a technologist who performs an imaging operation, an imaging radiation dose [mAs], and identification information of the subject. When the information indicating the decision result and the radiation image are output from the image decision unit 16, the imaging information unit 21 outputs the retained imaging information about the radiation image.

The imaging processing unit 22 is able to calculate a success rate of the imaging on the basis of the decision result of the image decision unit 16 and the identification information of the technologist, which is included in the imaging information, and store a calculation result in the storage unit 14. The storage unit 14 stores the success rate of the imaging on the basis of the calculation result of the imaging processing unit 22. The imaging processing unit 22 is able to perform processing for associating the imaging information output from the imaging information unit 21 with information indicating the radiation image output from the image decision unit 16 and the decision result of success or failure of imaging (success in imaging or failure in imaging) and store the resultant in the storage unit 14. Note that, this processing for association may be performed in the storage unit 14.

The display control unit 110 functions as a control unit that performs display control of the display unit 11. The display control unit 110 controls the display of the display unit 11 on the basis of an operation of the operation unit 12. For example, when the user operates the operation unit 12 arranged in the housing 19, in order to perform the display control in response to the operation, the display control unit 110 is able to read the radiation image, the decision result indicating success or failure of imaging (success in imaging or failure in imaging), the imaging information about the radiation image, and the information of the success rate of the imaging, which are stored in the storage unit 14, and display each of them on the display unit 11. The display control unit 110 is also able to generate a thumbnail image on the basis of the radiation image to display the thumbnail image on the display unit 11.

The display unit 11 is able to display the information indicating the decision result of the image decision unit 16 and the imaging information in association with each other. The display unit 11 is able to display, for example, the information indicating success or failure of imaging (success in imaging or failure in imaging) of the radiation image, the imaging information about the radiation image, and the thumbnail image of the radiation image under the display control by the display control unit 110. When the user operates the operation unit 12, the display control unit 110 acquires information from the storage unit 14 on the basis of an input from the operation unit 12, and performs display control such as scrolling or switching of the display of the display unit 11. In a case where a user operation through the operation rest unit 13 is input when the display of the display unit 11 is switched by a user operation through the operation unit 12, the display control unit 110 acquires information from the storage unit 14 and performs display control so as to return the display of the display unit 11 to a state before the switching.

When the radiation imaging apparatus 101 is connected to the information processing apparatus 102 through the communication unit 2 by wired communication or wireless communication, the overall control unit 1 of the radiation imaging apparatus 101 is able to acquire information stored in the storage unit 14 and transmit the information to the information processing apparatus 102 through the communication unit 2 of the radiation imaging apparatus 101. The information processing apparatus 102 is able to accumulate and process the information received from the radiation imaging apparatus 101. The information processing apparatus 102 is able to perform display control for displaying the information received from the radiation imaging apparatus 101 on the display unit 109 of the information processing apparatus 102.

When an error occurs in the radiation imaging apparatus 101, the error detection unit 111 detects an error occurrence part at which the error occurs, and inputs identification information (for example, such as an error code or an error number) for identifying the error occurrence part to the display control unit 110. When the identification information is input from the error detection unit 111, the display control unit 110 controls the display unit 11 to display the identification information input from the error detection unit 111. A prompt improvement is able to be performed when the occurrence of the error is notified to the user by displaying the identification information on the display unit 11.

When the aforementioned configuration of the imaging control apparatus 105 is provided inside the radiation imaging apparatus 101, the imaging control apparatus 105 functions as an imaging control unit that controls imaging of the radiation imaging apparatus 101. The imaging control unit is able to control imaging in a plurality of imaging modes. That is, the imaging control unit is able to control imaging by a first imaging mode or a second imaging mode while controlling each unit of the overall control unit 1 and the communication unit 2. The communication unit 2 is able to communicate with the external information processing apparatus through wired communication or wireless communication.

As the plurality of imaging modes, the imaging control unit is able to control imaging by the first imaging mode in which imaging is performed in a state of allowing communication with the external information processing apparatus through the communication unit 2 and a radiation image is displayed for each imaging on the display unit 11, or the second imaging mode in which imaging is performed in a state of not allowing communication with the external information processing apparatus through the communication unit 2 and a radiation image is stored in the storage unit 14. The storage unit 14, when the radiation imaging apparatus 101 performs the imaging in the first imaging mode, does not associate or store the radiation image and a decision result, and when the radiation imaging apparatus 101 performs the imaging in the second imaging mode, associates and stores the radiation image and the decision result of the image decision unit 16.

Figure 5:
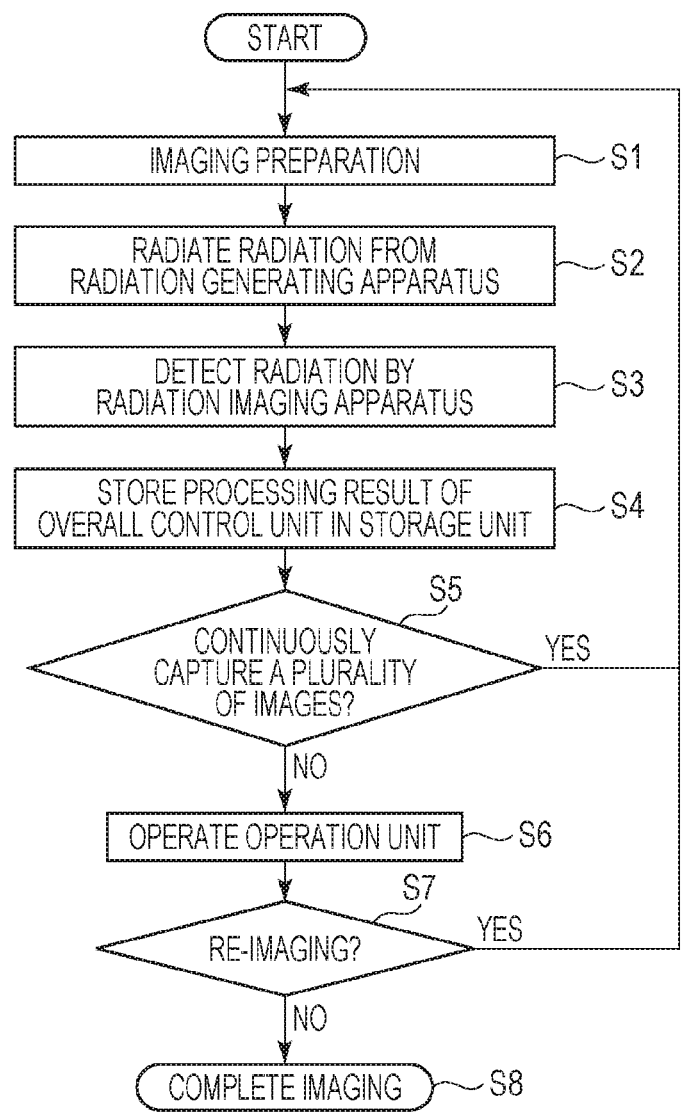
FIG. 5 is a flowchart for explaining imaging processing by the radiation imaging apparatus according to one or more aspects of the present disclosure.

FIG. 5 is a flowchart for explaining imaging processing by the radiation imaging apparatus 101 according to the present exemplary embodiment. A user performs imaging preparation at step S1. With the imaging preparation, the radiation imaging apparatus 101 is set in an imaging enable state and a positional relationship among the radiation generating apparatus 106, the subject H, and the radiation imaging apparatus 101 is adjusted to be appropriate to a portion to be imaged. With the imaging preparation by the user, the positional relationship among the radiation imaging apparatus 101, the subject H, and the radiation generating apparatus 106 as illustrated in FIG. 1 is provided.

After the imaging preparation is completed, the radiation generating apparatus 106 radiates the radiation 107 to the subject H at step S2. Then, the radiation detection unit 15 of the radiation imaging apparatus 101 detects the radiation 107 transmitted through the subject H at step S3. The radiation detection unit 15 detects the radiation 107, which is transmitted through the subject H, as an image signal (electric charge). The photoelectric conversion element of each of the pixels 200 constituting the radiation detection unit 15 converts light, which is converted by a phosphor, into an image signal (electric charge) as an electric signal, and the image signal (electric charge) is accumulated in the capacitor of each of the pixels 200.

A processing result of the overall control unit 1 is stored in the storage unit 14 at step S4. The reading unit 17 reads the image signal (electric charge) from each of the pixels 200 in accordance with an instruction from the overall control unit 1. The reading unit 17 outputs the image signal (electric charge) read from the pixel 200 to the overall control unit 1 through the A/D conversion unit 7. The image decision unit 16 of the overall control unit 1 performs decision processing for deciding whether a radiation image meets a predetermined decision criterion, and outputs information indicating a decision result of success or failure of imaging of the radiation image and the radiation image in association with each other. The imaging processing unit 22 of the overall control unit 1 performs, on the basis of the information output from the image decision unit 16 and the imaging information unit 21, processing for associating information indicating the radiation image and the decision result of success or failure of the imaging with imaging information about the radiation image and stores them in the storage unit 14. Note that, this processing for association may be performed in the storage unit 14.

When a plurality of images of the subject H are continuously captured at step S5, (continuous capturing of a plurality of images: S5—Yes), the procedure is returned to step S1 and similar processing is repeated. On the other hand, when one image of the subject H is captured (S5—No), the procedure proceeds to step S6.

At step S6, the user operates the operation unit 12 in the radiation imaging apparatus 101 in order to check the decision result of the image decision unit 16. Then, at step S7, the user checks the display of the display unit 11 while operating the operation unit 12 to check the decision result of the image decision unit 16. When the user operates the operation unit 12, the display control unit 110 acquires information from the storage unit 14 on the basis of an input from the operation unit 12 and performs display control such as scrolling or switching of the display of the display unit 11. The user is able to check identification information of the radiation image, imaging information such as an imaging time and a portion to be imaged, and information of a decision result indicating success or failure of imaging (success in imaging or failure in imaging). At this time, when the image decision unit 16 decides that the imaging has failed, the procedure returns to step S1 to perform the imaging, which has failed, again (S7—Yes) and similar processing is repeated. The user operates the operation reset unit 13 to return the display of the display unit 11 to a state before the operation. On the other hand, when the imaging has succeeded at step S7, re-imaging is not performed (S7—No) and the imaging processing is finished at step S8.

FIG. 6 illustrates an example of association of imaging information with information indicating a decision result (decision result indicating success or failure of imaging (success in imaging or failure in imaging) of a radiation image) of the radiation image. A first line of FIG. 6 corresponds to a first captured image (identification information of the image=image 1). In imaging information of the image 1, a portion to be imaged is a chest front, the number of times of imaging (counter) is 001, and a decision result of the radiation image is success in imaging. An imaging time is eleven, identification information of a technologist is 001, and an imaging radiation dose is 10 [mAs]. The information associated as illustrated in FIG. 6 is stored in the storage unit 14. The storage unit 14 associates and stores the radiation image and the decision result of the image decision unit 16. Moreover, the storage unit 14 associates and stores the radiation image, the decision result of the image decision unit 16, and imaging information including an imaging condition of the radiation image.

When the user operates the operation unit 12, the display control unit 110 acquires information from the storage unit 14 and controls the display of the display unit 11 on the basis of the acquired information. According to the configuration of the radiation imaging apparatus 101 of the present exemplary embodiment, a technologist who is a user is able to check success or failure of imaging by the display of the display unit 11 of the radiation imaging apparatus 101 without transmitting information to the information processing apparatus 102. That is, the user is able to obtain the decision result of success or failure of imaging of the radiation image whether or not to visually check the radiation image.

The display control unit 110 causes the display unit 11 to display the decision result of the image decision unit 16 in a distinguishable display format. FIGS. 7A and 7B each illustrates a display example of the display unit 11. When the user operates the operation unit 12, desired information is displayed on the display unit 11. Each of the display examples of FIGS. 7A and 7B indicates an example in which imaging of an image 3 has failed. When imaging information is associated with an image (image 3 in each example of FIGS. 7A and 7B) imaging of which has failed, the display control unit 110 performs display control for notifying that the imaging has failed. The display control unit 110 is able to cause the display unit 11 to display information indicating the decision result of the image decision unit 16, which indicates failure of imaging, and imaging information associated with the information indicating the decision result with display colors thereof changed. FIG. 7A illustrates an example of display control for changing a color of the display of the display unit 11, in which it is notified that imaging has failed by inverting a background of the display corresponding to the image 3 from white to black for display and highlighting characters and numerical values by making them void.

The display control unit 110 is also able to cause the display unit 11 to display the information indicating the decision result of the image decision unit 16, which indicates that imaging has failed, and the imaging information associated with the information indicating the decision result with display fonts thereof changed. FIG. 7B illustrates an example of display control for changing a display font, in which it is notified that imaging has failed by displaying characters and numerical values corresponding to the image 3 in bold and increasing display sizes thereof for highlighting.

Note that, the display control for notifying failure of imaging is not limited to the display examples of FIGS. 7A and 7B, and it is also possible to visually notify that imaging has failed, for example, by flashing a display of information of characters and numerical values corresponding to the image 3, changing a display font to italics, or displaying an exclamation mark in combination with a display content. The display control unit 110 is also able to cause the display unit 11 to display the information indicating the decision result of the image decision unit 16, which indicates that imaging has failed, and the imaging information associated with the information indicating the decision result in combination with an identification mark for notifying failure of imaging.

Further, the display control unit 110 is able to cause the display unit 11 to display information indicating the decision result of the image decision unit 16, which indicates that imaging has succeeded, and imaging information associated with the information indicating the decision result in combination with a thumbnail image of the radiation image. For the image, imaging of which has failed, the display control unit 110 is also able to cause the display unit 11 to display information indicating the decision result of the image decision unit 16, which indicates that imaging has failed, and the imaging information associated with the information indicating the decision result without combining with a display of the thumbnail image of the radiation image.

The association of the radiation image with the decision result is able to be carried out in any mode of the plurality of imaging modes in the radiation imaging system 100 in the present exemplary embodiment. Note that, the information processing apparatus 102 may be set so as not to perform the association in the first imaging mode but performs the association only in the second imaging mode. In the second imaging mode, a radiation image is transferred to the information processing apparatus 102 for each imaging and the radiation image is not displayed, so that visual decision is not able to be performed. Thus, by associating the radiation image and the decision result for each imaging, quality of the radiation image can be decided later. In addition, in the first imaging mode, the association is not performed, so that the processing is reduced, thus making it possible to display the radiation image on the display unit 109 more promptly.

According to the present exemplary embodiment, it is possible to obtain a decision result of success or failure of imaging of a radiation image whether or not a user visually checks the radiation image. It is also possible to obtain a decision result of success or failure of imaging of a plurality of radiation images without connection to the information processing apparatus 102, thus making it possible to reduce burden on the user and perform imaging of the radiation images efficiently. By associating and storing a decision result of success or failure of imaging of a radiation image and the radiation image, it is possible, after acquiring a plurality of radiation images, to utilize, for display, that which of the plurality of radiation images has failed in imaging or succeeded in imaging.

Second Exemplary Embodiment

Figure 9:
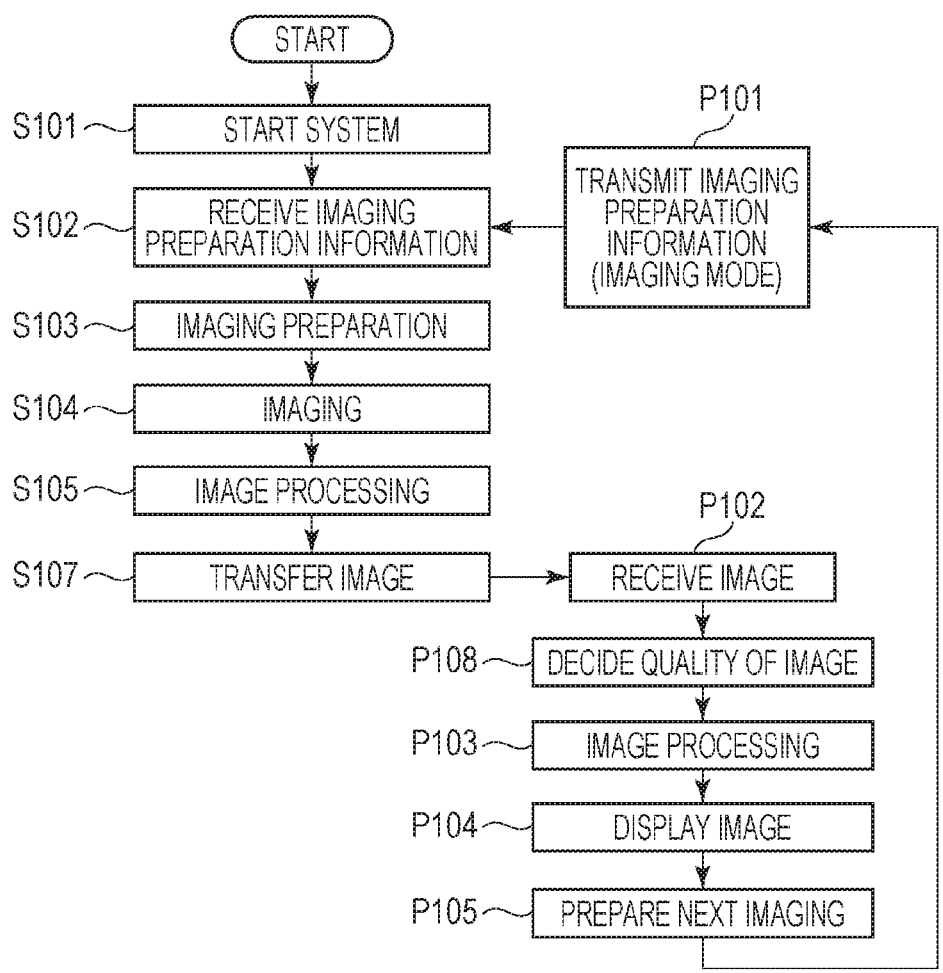
FIG. 9 is a flowchart illustrating an operation of the radiation imaging system according to one or more aspects of the present.

FIGS. 8 and 9 are flowcharts each indicating an operation of a radiation imaging system according to a second exemplary embodiment. The operation of the radiation imaging system in the second exemplary embodiment will be described below with reference to the flowcharts. Note that, in FIGS. 8 and 9, a step whose first letter of a step number is S indicates an operation executed by the radiation imaging apparatus and a step whose first letter is P indicates an operation executed by the information processing apparatus. FIG. 8 illustrates the flowchart when the second imaging mode is selected and FIG. 9 illustrates the flowchart when the first imaging mode is selected.

First, the operation of the radiation imaging system according to the second exemplary embodiment will be described with reference to FIG. 8.

First, power source supply to each unit of the radiation imaging apparatus 101 is started as a start-up operation (S101). The radiation imaging apparatus 101 is set, for example, to be connected to the radiation generating apparatus 106 and the information processing apparatus 102.

Next, description will be given for P101. At P101, an input of imaging preparation information is performed to the information processing apparatus 102. This input is performed through the operation unit 115. The information processing apparatus 102 then transmits the imaging preparation information, which is input, to the radiation imaging apparatus 101. The imaging preparation information includes information about a subject to be imaged, information about a portion to be imaged, and information about a condition of generating radiation. The imaging preparation information also includes information about image quality decision performed by the radiation imaging apparatus 101. The information about image quality decision can include, for example, a type of image quality decision, an imaging mode, a decision criterion, and the like.

The radiation imaging apparatus 101 receives the imaging preparation information (S102), and then performs imaging preparation (S103). Here, the radiation imaging apparatus 101 prepares for imaging on the basis of an imaging mode received from the information processing apparatus 102 of the plurality of imaging modes. When the first imaging mode is specified, the radiation imaging apparatus 101 performs setting so as not to perform image quality decision. On the other hand, when the second imaging mode is specified, the radiation imaging apparatus 101 performs quality decision of a radiation image with the following flowchart.

The radiation imaging apparatus 101 performs control so as to perform preparation driving of the radiation detection unit 15 as the imaging preparation. The preparation driving is an operation for bringing into a state where the radiation imaging apparatus 101 is ready to perform imaging, and can include an operation for discharging accumulated electric signals of the pixels 200 of the radiation detection unit 15. The user adjusts a positional relationship among a subject, the radiation imaging apparatus 101, and a radiation source at the step of imaging preparation. Further, the user performs, for example, an input of an imaging condition to the radiation generating apparatus 106. Note that, the positional relationship may be automatically adjusted on the basis of an input result of the imaging condition to the radiation generating apparatus 106.

As an operation for imaging, the radiation imaging apparatus 101 acquires digital image data on the basis of the radiated radiation (S104). Specifically, the radiation detection unit 15 converts the radiation, which is radiated from the radiation generating apparatus 106 and transmitted through the subject, into an electric charge. The converted electric charge is converted into digital data by the reading unit 17 and transmitted to the overall control unit 1.

The overall control unit 1 applies image processing to the digital data (radiation image data) (S105). The overall control unit 1 performs offset correction and gain correction as the image processing. Data saved in the storage unit 14 is used as various data for the gain correction. Note that, the overall control unit 1 is also able to perform the image processing collectively for digital data corresponding to all the pixels or execute the image processing for each radiation image data which is obtained by dividing or reducing the digital data and couple the radiation image data later.

After performing the image processing, the overall control unit 1 performs image quality decision of (image quality judgment) by the image decision unit 16 (S106). In this case, it is decided whether the captured image has a level sufficiently usable for the purpose of a diagnosis or the like. In the present exemplary embodiment, the image decision unit 16 performs level decision and body movement detection.

Next, a difference of processing based on a result of the image quality decision will be described. First, a case where the radiation imaging apparatus 101 decides that there is no problem in radiation image data, which is captured, as a result of the image quality decision, will be described. In this case, the radiation image data is transferred to the image processing apparatus 102 (S107). The information processing apparatus 102 receives the radiation image data (P102), and then performs additional image processing (P103). The information processing apparatus 102 performs control so as to display an image after the image processing on the display unit 109. The user is able to check the displayed image and make various diagnoses and the like (P104). Information for next imaging is input from the operation unit 115 to the information processing apparatus 102 (P105). Upon the input of the information for the next imaging, the information processing apparatus 102 shifts to processing P101.

Next, a case where the radiation imaging apparatus 101 decides that there may be some problem in the captured image as a result of the image quality decision will be described. In this case, the radiation imaging apparatus 101 notifies that the result of the image quality decision is not good in a distinguishable manner. The radiation imaging apparatus 101 can cause the display unit 11 to display that the radiation image may be inappropriate. Note that, the radiation imaging apparatus 101 may perform the notification to the user in a distinguishable manner by sound or vibration while displaying such a display on the display unit 11.

The radiation imaging apparatus 101 causes the display unit 11 to perform a display, as illustrated in FIG. 6, for making the user select whether to perform re-imaging (S109). When selecting whether to perform re-imaging, the user selects Y or N with a cursor button of the operation unit and presses a confirm/reset button.

Here, when it is selected to perform re-imaging (Y is selected), the radiation imaging apparatus 101 transmits, to the information processing apparatus 102, the result of the image quality decision and data to which information indicating that re-imaging is performed is added (S111). Note that, the radiation imaging apparatus 101 may further add information indicating that the radiation image is a rejected image and a reason therefor to the data whose result of the image quality decision is not good.

When the information processing apparatus 102 receives the data to which the information indicating that re-imaging is performed is added (P106), preparation for re-imaging is started immediately and imaging preparation information under the same condition as that of the previous imaging is transmitted to the radiation imaging apparatus 101. Thus, when it is decided that the radiation image is inappropriate as a result of the image quality decision, the information processing apparatus 102 is able to immediately make preparation for re-imaging and perform a preparation operation for re-imaging.

On the other hand, when it is selected not to perform re-imaging (N is selected), the radiation imaging apparatus 101 transfers, to the information processing apparatus 102, the radiation image and the radiation image to which the result of the image quality decision is added. In this case, the information processing apparatus 102 sequentially performs the processing from P102 to P105 similarly to a case where an appropriate image is transferred. When causing the display unit 109 to display the radiation image, the information processing apparatus 102 displays a display indicating that there is a possibility that the radiation image includes a problem of quality together on the display unit 109. Thus, the user is able to visually check the radiation image and the display about the result of the image quality decision, which are displayed on the display unit 109, and determine whether or not to perform re-imaging. After that, the information processing apparatus 102 performs setting for re-imaging. Note that, in a case where an image to which information indicating that the image is inappropriate is added is transferred as a result of the image quality decision while display control of the image is performed, the information processing apparatus 102 may perform control to automatically make setting for re-imaging.

Note that, a decision item of the image quality decision and a decision criterion are set from the information processing apparatus 102, but may be set by an operation from the operation unit 12 of the radiation imaging apparatus 101. In the present flowchart, the image decision unit 16 executes two quality decisions for a radiation image, but may perform one quality decision or select three or more processing. Further, the information processing apparatus 102 may perform image quality decision after processing is performed inside the radiation imaging apparatus 101. At this time, the decision item of image quality decision performed by the radiation imaging apparatus 101 and a decision item of image quality decision performed by the information processing apparatus 102 may be different or the same. When the information processing apparatus 102 performs image quality decision, the information processing apparatus 102 functions as a second decision unit which is a decision unit different from the radiation imaging apparatus 101. Alternatively, when the radiation imaging apparatus 101 and the information processing apparatus 102 carry out different decision items, it is desired that the item by which quality of an image can be decided at minimum is carried out by the radiation imaging apparatus 101 and auxiliary quality decision for visually making a diagnosis about an image is carried out by the information processing apparatus 102.

The information processing apparatus 102 specifies the decision of image quality decision with any combination of a portion to be imaged, an imaging condition, and the like, and manages the combination as an imaging protocol.

Next, the flowchart of the radiation imaging system when the second imaging mode is specified will be described with reference to FIG. 9. The radiation imaging apparatus 101 performs the predetermined imaging processing at S105, and then immediately transfers the radiation image to the information processing apparatus 102 (S107).

The information processing apparatus 102 then receives the radiation image (P102), and performs quality decision for the transferred radiation image at P108. The information processing apparatus 102 may immediately display the radiation image on the display unit 109 without performing quality decision for the radiation image. In this case, the user can check the radiation image promptly and hence can easily perform visual judgement.

Description has been given above for the case where quality decision for a radiation image is performed in the radiation imaging system in which imaging is able to be performed in an imaging mode selected from the plurality of imaging modes in the second exemplary embodiment. The first imaging mode is based on a system in which imaging is performed in a state where the radiation imaging apparatus and the information processing apparatus are able to communicate with each other. Further, since the radiation imaging apparatus transfers a radiation image for each imaging, decision processing is not performed inside the radiation imaging apparatus and the radiation image is immediately displayed, so that diagnostic efficiency is improved. On the other hand, the second imaging mode is based on a system in which imaging is performed in a state where the radiation imaging apparatus and the information processing apparatus are not able to communicate with each other. Further, the radiation imaging apparatus stores a radiation image in the storage unit and continuously captures a plurality of images in the second imaging mode. Thus, the user is not able to visually check the radiation image for each imaging. Accordingly, it is possible to perform quality decision for the radiation image efficiently by performing quality decision for the radiation image inside the radiation imaging apparatus in the second imaging mode.

The configuration of the present exemplary embodiment makes it possible to decide quality of a radiation image appropriately in accordance with an imaging mode.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

While the present disclosure has been described with reference to exemplary embodiments, the scope of the following claims are to be accorded the broadest interpretation so as to encompass all such modifications and equivalent structures and functions.

This application claims the benefit of Japanese Patent Application No. 2015-244651 filed Dec. 15, 2015, and Japanese Patent Application No. 2015-248028 filed Dec. 18, 2015, which are hereby incorporated by reference herein in their entirety.

What is claimed is:

1. A radiation imaging system, comprising:
a radiation imaging apparatus including
a radiation detection unit configured to acquire a radiation image by imaging;
a decision unit configured to decide whether or not the radiation image meets a decision criterion of success or failure of the imaging;
a storage unit configured to associate and store the radiation image and a decision result; and
an information processing apparatus configured to communicate with the radiation imaging apparatus using wired or wireless communication,
wherein the radiation imaging apparatus further includes a control unit configured to control the imaging in a plurality of imaging modes,
wherein the control unit is configured to control the imaging in a first imaging mode in which the acquired radiation image is transmitted to the information processing apparatus each time the radiation image is acquired by the imaging, and a second imaging mode in which the acquired radiation image is stored in the storage unit without being transmitted to the information processing apparatus each time the radiation image is acquired by the imaging, and
wherein, in a case where the imaging is performed in the first imaging mode, the storage unit does not associate or store the radiation image and the decision result while the information processing apparatus associates the radiation image with the decision result, and in a case where the imaging is performed in the second mode, the storage unit associates and stores the radiation image and the decision result while the information processing apparatus does not associate the radiation image with the decision result.

2. The radiation imaging system according to claim 1, wherein the storage unit associates and stores the radiation image, the decision result of the decision unit, and imaging information including an imaging condition of the radiation image.

3. The radiation imaging system according to claim 1, wherein, when a plurality of radiation images is acquired by the radiation detection unit, the storage unit associates and stores the plurality of radiation images and the decision result for each of the plurality of radiation images.

4. The radiation imaging system according to claim 1, wherein the radiation detection unit starts acquisition of the radiation image on the basis of detection of radiated radiation.

5. The radiation imaging system according to claim 2, wherein the radiation imaging apparatus further includes:
a display unit configured to display the decision result of the decision unit and the imaging information in association with each other;
an operation unit configured to receive an operation for switching a display of the display unit; and
a display control unit configured to control the display of the display unit on the basis of an operation of the operation unit.

6. The radiation imaging system according to claim 5, wherein the decision unit decides that the imaging has succeeded when the radiation image meets the decision criterion, and decides that the imaging has failed when the radiation image does not meet the decision criterion, and wherein the display control unit causes the display unit to display the decision result of the decision unit in a distinguishable display format.

7. The radiation imaging system according to claim 5, further comprising:
an imaging information unit configured to retain imaging information about the acquired radiation image,
wherein the imaging information includes at least any one of identification information of the radiation image, a portion of a subject to be imaged, the number of times of imaging, an imaging time, identification information of a technologist performing an imaging operation, an imaging radiation dose, and identification information of the subject.

8. The radiation imaging system according to claim 5, further comprising:
an error detection unit configured to detect an error occurrence part at which an error occurs, and input identification information for identifying the error occurrence part to the display control unit,
wherein the display control unit controls the display unit to display the identification information input from the error detection unit.

9. The radiation imaging system according to claim 5, further comprising:
a communication unit configured to communicate with the information processing apparatus using wired or wireless communication.

10. The radiation imaging system according to claim 6, wherein the display control unit causes the display unit to display the decision result of the decision unit, which indicates failure of the imaging, and the imaging information associated with the decision result with display colors thereof changed.

11. The radiation imaging system according to claim 6, wherein the display control unit causes the display unit to display the decision result of the decision unit, which indicates failure of the imaging, and the imaging information associated with the decision result with display fonts thereof changed.

12. The radiation imaging system according to claim 6, wherein the display control unit causes the display unit to display the decision result of the decision unit, which indicates failure of the imaging, and the imaging information associated with the decision result in combination with an identification mark for notifying the failure of the imaging.

13. The radiation imaging system according to claim 6, wherein the display control unit causes the display unit to display the decision result of the decision unit, which indicates success of the imaging, and the imaging information associated with the decision result in combination with a thumbnail image of the radiation image.

14. The radiation imaging system according to claim 13, wherein, for an image the imaging of which has failed, the display control unit causes the display unit to display the decision result of the decision unit, which indicates failure of the imaging, and the imaging information associated with the decision result without combining a display of the thumbnail image of the radiation image.

15. The radiation imaging system according to claim 7, further comprising an imaging processing unit configured to calculate a success rate of imaging on the basis of the decision result of the decision unit and the identification information of the technologist, which is included in the imaging information, and store a calculation result in the storage unit.

16. The radiation imaging system according to claim 15, wherein the storage unit stores the success rate of imaging on the basis of the calculation result of the imaging processing unit, and
wherein the display control unit causes the display unit to display the success rate of imaging stored in the storage unit.

17. The radiation imaging system according to claim 3, wherein the storage unit associates and stores the plurality of radiation images, the decision result of the decision unit for each of the plurality of radiation images, and imaging information for each of the plurality of radiation images.

18. A control method for a radiation imaging system that includes a radiation imaging apparatus including a radiation detection unit configured to acquire a radiation image by imaging, a decision unit configured to decide whether or not the radiation image meets a decision criterion of success or failure of the imaging, and a storage unit configured to associate and store the radiation image and a decision result, and an information processing apparatus configured to communicate with the radiation imaging apparatus using wired or wireless communication, the control method comprising:
deciding, by the decision unit, whether or not the radiation image meets the decision criterion for deciding success or failure of the imaging; and
storing the radiation image and the decision result in the storage unit in association with each other,
wherein the radiation imaging apparatus further includes a control unit configured to control the imaging in a plurality of imaging modes,
wherein the control unit is configured to control the imaging in a first imaging mode in which the acquired radiation image is transmitted to the information processing apparatus each time the radiation image is acquired by the imaging, and a second imaging mode in which the acquired radiation image is stored in the storage unit without being transmitted to the information processing apparatus each time the radiation image is acquired by the imaging, and
wherein, in a case where the imaging is performed in the first imaging mode in the storing, the storage unit does not associate or store the radiation image and the decision result while the information processing apparatus associates the radiation image with the decision result, and in a case where the imaging is performed in the second mode in the storing, the storage unit associates and stores the radiation image and the decision result while the information processing apparatus does not associate the radiation image with the decision result.

19. A non-transitory recording medium having a program stored therein for causing a computer to execute the control method for the radiation imaging system according to claim 18.

* * * * *